United States Patent
Essen-Moller

Patent Number: 5,810,741
Date of Patent: *Sep. 22, 1998

[54] METHOD OF MEASURING RESPIRATION AND RESPIRATORY EFFORT USING PLURAL CATHETERS

[75] Inventor: Anders Essen-Moller, Stockholm, Sweden

[73] Assignee: Synectics Medical AB, Sweden

[*] Notice: The term of this patent shall not extend beyond the expiration date of Pat. No. 5,477,860.

[21] Appl. No.: 576,034

[22] Filed: Dec. 21, 1995

Related U.S. Application Data

[63] Continuation-in-part of Ser. No. 972,208, Nov. 5, 1992, Pat. No. 5,477,860.

[51] Int. Cl.$^6$ ........................................... A61B 5/08
[52] U.S. Cl. ................................................... 600/529
[58] Field of Search .................... 128/716–725, 128/730, 207.14, 207.15, 207.18, 204.23; 600/529–534, 543

[56] References Cited

U.S. PATENT DOCUMENTS

| | | |
|---|---|---|
| 2,162,656 | 6/1939 | Warrington . |
| 2,168,867 | 8/1939 | George, III . |
| 2,857,915 | 10/1958 | Sheridan . |
| 3,373,735 | 3/1968 | Gallagher . |
| 3,480,003 | 11/1969 | Crites . |
| 3,669,095 | 6/1972 | Kobayashi et al. . |
| 3,690,309 | 9/1972 | Pluzhnikov et al. . |
| 3,817,241 | 6/1974 | Grausz . |
| 3,905,889 | 9/1975 | Macur et al. . |
| 3,923,626 | 12/1975 | Niedrach et al. . |

(List continued on next page.)

FOREIGN PATENT DOCUMENTS

| | | |
|---|---|---|
| 0073558 | 3/1983 | European Pat. Off. . |
| 0080680 | 6/1983 | European Pat. Off. . |
| 0 241 644 | 1/1987 | European Pat. Off. . |
| 0356603 | 11/1993 | European Pat. Off. . |
| 79-09689 | 11/1980 | France . |
| 2 162 656 | 6/1973 | Germany . |
| 2162656 | 6/1973 | Germany . |
| 3140265 | 4/1983 | Germany . |
| 221635 | 5/1985 | Germany . |
| 35 23 987 | 7/1985 | Germany . |
| 7707275 | 1/1979 | Netherlands . |
| 178028 | 11/1966 | U.S.S.R. . |
| 272477 | 5/1968 | U.S.S.R. . |
| 1502004 | 8/1989 | U.S.S.R. . |

OTHER PUBLICATIONS

DeMeester, American Association for The Study of Live Diseases, "Ambulatory Monitoring of Gastric Emptying", May 16, 1993, Abstract.

"Clinical relevance of ambulatory 24–hour . . .", Vogten, et al., 1987, pp. 21–31 in Netherlands Journal of Medicine.

Computerized Axial Manometry of the Esophagus, Bombeck, et al. in Annals of Surgery, vol. 206, No. 4, pp. 465–472, Oct. 1987.

(List continued on next page.)

*Primary Examiner*—Jennifer Bahr
*Assistant Examiner*—Samuel Gilbert
*Attorney, Agent, or Firm*—Pillsbury Madison & Sutro LLP; Stephen C. Glazier

[57] ABSTRACT

A method of determining the existence and location of an obstruction in a respiratory track includes introducing a first catheter having a first sensing site into the body of a patient until the first sensing site is positioned so that it is distal to the obstruction. The first catheter is used to monitor respiratory effort with generated signals indicative of respiratory effort. A second catheter having a second sensing site is positioned so that the second sensing site is near the nostrils. The second catheter is used to monitor actual respiration with generated signals indicative of actual respiration. The existence of the obstruction is verified by observing respiratory effort signals without corresponding actual respiration signals.

13 Claims, 3 Drawing Sheets

U.S. PATENT DOCUMENTS

| | | |
|---|---|---|
| 4,016,866 | 4/1977 | Lawton . |
| 4,063,548 | 12/1977 | Klatt et al. . |
| 4,073,287 | 2/1978 | Bradley et al. . |
| 4,119,498 | 10/1978 | Edwall et al. . |
| 4,176,659 | 12/1979 | Rolfe . |
| 4,197,852 | 4/1980 | Schindler et al. . |
| 4,208,588 | 6/1980 | Rudin . |
| 4,214,593 | 7/1980 | Imbruce et al. . |
| 4,265,249 | 5/1981 | Schindler et al. . |
| 4,299,929 | 11/1981 | Sakano et al. . |
| 4,381,011 | 4/1983 | Somers, III . |
| 4,442,841 | 4/1984 | Uehara et al. . |
| 4,471,779 | 9/1984 | Antoshkiw et al. . |
| 4,476,871 | 10/1984 | Hon . |
| 4,478,222 | 10/1984 | Koning et al. . |
| 4,486,290 | 12/1984 | Cahalan et al. . |
| 4,487,206 | 12/1984 | Aagard . |
| 4,503,859 | 3/1985 | Petty et al. . |
| 4,508,103 | 4/1985 | Calisi . |
| 4,577,640 | 3/1986 | Hofmeister . |
| 4,593,701 | 6/1986 | Kobayashi et al. . |
| 4,600,015 | 7/1986 | Evans et al. . |
| 4,618,929 | 10/1986 | Miller et al. . |
| 4,631,061 | 12/1986 | Martin . |
| 4,632,119 | 12/1986 | Reichstein . |
| 4,642,104 | 2/1987 | Sakamoto et al. . |
| 4,655,225 | 4/1987 | Dahne et al. . |
| 4,681,116 | 7/1987 | Settler . |
| 4,682,596 | 7/1987 | Bales et al. . |
| 4,691,708 | 9/1987 | Kane . |
| 4,696,672 | 9/1987 | Mochizuki et al. . |
| 4,700,709 | 10/1987 | Kraig . |
| 4,700,799 | 10/1987 | Kawano . |
| 4,703,757 | 11/1987 | Cohen . |
| 4,705,503 | 11/1987 | Dorman et al. . |
| 4,729,384 | 3/1988 | Bazenet . |
| 4,748,113 | 5/1988 | Marshall . |
| 4,748,562 | 5/1988 | Miller et al. . |
| 4,757,194 | 7/1988 | Simms . |
| 4,776,347 | 10/1988 | Matthews . |
| 4,796,629 | 1/1989 | Grayzel . |
| 4,803,992 | 2/1989 | Lemelson . |
| 4,815,471 | 3/1989 | Stobie . |
| 4,834,101 | 5/1989 | Collison et al. . |
| 4,850,371 | 7/1989 | Broadhurst . |
| 4,873,990 | 10/1989 | Holmes et al. . |
| 4,887,610 | 12/1989 | Mittal . |
| 4,892,101 | 1/1990 | Cheung et al. . |
| 4,901,731 | 2/1990 | Millar . |
| 4,924,877 | 5/1990 | Brooks . |
| 4,966,161 | 10/1990 | Wallace et al. . |
| 4,975,581 | 12/1990 | Robinson et al. . |
| 4,976,265 | 12/1990 | Falcial et al. . |
| 4,981,470 | 1/1991 | Bombeck, IV . |
| 4,986,671 | 1/1991 | Sun et al. . |
| 4,991,590 | 2/1991 | Shi . |
| 4,996,161 | 2/1991 | Conners et al. . |
| 5,005,584 | 4/1991 | Little . |
| 5,007,427 | 4/1991 | Suzuki et al. . |
| 5,018,529 | 5/1991 | Tenerz . |
| 5,022,396 | 6/1991 | Watanabe . |
| 5,025,786 | 6/1991 | Siegel . |
| 5,046,497 | 9/1991 | Millar . |
| 5,047,627 | 9/1991 | Yim et al. . |
| 5,054,487 | 10/1991 | Clarke . |
| 5,103,835 | 4/1992 | Yamada et al. . |
| 5,105,812 | 4/1992 | Corman . |
| 5,108,364 | 4/1992 | Takezawa et al. . |
| 5,117,827 | 6/1992 | Stuebe et al. . |
| 5,119,498 | 6/1992 | McNeill et al. . |
| 5,151,598 | 9/1992 | Denen . |
| 5,158,083 | 10/1992 | Sacristan et al. . |
| 5,184,619 | 2/1993 | Austin . |
| 5,199,443 | 4/1993 | Maurer et al. . |
| 5,207,226 | 5/1993 | Bailin et al. . |
| 5,222,594 | 6/1993 | Sumino . |
| 5,280,786 | 1/1994 | Wlodarczyk et al. . |
| 5,291,884 | 3/1994 | Heinemann et al. . |
| 5,301,673 | 4/1994 | Rabito et al. . |
| 5,314,804 | 5/1994 | Boguslaski et al. . |
| 5,477,860 | 12/1995 | Essen-Moller ........................... 128/716 |
| 5,546,952 | 8/1996 | Erickson ................................ 128/716 |
| 5,605,151 | 2/1997 | Lynn .................................. 128/716 X |

OTHER PUBLICATIONS

"The laser motility sensor for long–term study of intraesophageal pressure", Schneider et al., in Primary Motility Disorder of the Esophagus, Giuli et al., eds., pp. 64–69 1991.

Kim et al., American Journal of Clinical Pathology, 1990, vol. 94, pp. 187–191, The Gastric Juice Urea and Ammonia . . . .

Butcher et al., Digestion, 1992, vol. 53, pp. 142–148, Use of an Ammonia Electrode for Rapid Quantification of Helicobacter pylori Urease: Its use in the Endoscopy Room an in the. . .

The New Yorker, Sep. 20, 1993, T. Monmaney, "Marshalls's Hunch".

"Oesophageal multipurpose monitoring probe", Baker et al., World Wide Patent Monocrystant . . . . (Brochure).

Digestive Diseases, Reprint, vol. 8, Suppl. 1, pp. 60–70, 1990, Scarpignato et al., "Simultaneous Measurement and Recording. . ".

Hojgaard et al., "A New Method for Measurement of the Electrical Potential Difference Across the Stomach Wall", 1991 pp. 847–858.

METHOD OF MEASURING RESPIRATION AND RESPIRATORY EFFORT USING PLURAL CATHETERS

This is a continuation-in-part of U.S. patent application Ser. No. 07/972,208, filed Nov. 5, 1992 now U.S. Pat. No. 5,477,860.

BACKGROUND OF THE INVENTION

1. Field of the Invention

The present invention relates to catheters that monitor respiration and respiratory effort. More particularly, the present invention relates to devices that monitor inhalation pressures related to respiration in patients and, specifically, in the study of sleep apnea.

Catheters are well known in medicine and a wide variety exist for a variety of purposes. Catheters are typically flexible tubes of varying sizes that are inserted into the body. One common application of catheters, for example, is the removal of bodily fluids from the bladder during a time when the patient is incapacitated. As the technology of medicine has expanded, catheters are becoming more widely used for a greater variety of purposes.

Catheters exist that have pressure sensors at the distal tip. When these pressure sensors are inserted into the body, the local pressure around the distal tip of the catheter is able to be measured. In general, these prior art pressure sensors are usually used to measure the pressure of solid body parts against the catheter, and not air pressure in spaces filled with air.

Catheters also exist that have, on their distal ends, pH sensors. In these types of catheters, an electrical wire runs inside the catheter to the proximal end of the catheter. When the catheter is inserted into the body, this arrangement permits the electrical sensing of pH (that is, acidity) of the immediate environment of the distal tip. Such pH-catheters are presently manufactured by Synectics Medical AB of Sweden and distributed in the U.S. by Synectics Medical, Inc. of 1425 Greenway Drive, Suite 600, Irving, Tex.

A lumen is a channel inside the catheter that runs the length of the catheter. Multiple lumen catheters are well known. These catheters can function much like multiple catheters with each lumen dedicated to one function. As such, a single catheter with multiple lumens can operate as a multiple function catheter. Since the diameter of the catheter is of critical importance, it becomes difficult to incorporate a large number of lumens within a single catheter. The restriction of space availability inhibits the ability to incorporate many functions into one catheter.

2. Description of Related Art

Several methods are known that attempt to measure the degree of effort a patient is exerting in an attempt to breathe. The degree of effort exerted in the attempt to breathe is identified as "respiratory effort". Such methods include applying stretch sensitive belts (similar to strain gauges) to the outside of the abdomen, or the application of electrodes to the chest to measure changes in impedance. These approaches are cumbersome and inaccurate. The most accurate technique for measuring respiratory effort is through measuring air pressure changes in the esophagus or stomach. An effort to inhale results in an air pressure drop in the esophagus and trachea, and in a pressure increase in the stomach. This happens even though real inspiration and movement of air from the ambient room to the patient's lungs may not necessarily follow due to, for example, pharyngeal obstruction. An effort to exhale causes analogous events, but in the opposite directions (that is, an air pressure increase in the esophagus and trachea, and a drop in the stomach). When no effort to breathe occurs, the air pressure in these areas will remain constant.

The prior art in the area of respiratory effort in the esophagus includes placing a balloon made from the finger of a latex glove on the end of an esophageal catheter. The balloon is then partially inflated. An air pressure monitor at the proximal end of the catheter connected to the balloon indicates respiratory effort. The relatively large size of the balloon often interferes with the esophageal function and other simultaneous intraesophageal catheterizations. Prior art includes using a small balloon fixed to a piece of tubing and connected to an exterior pressure transducer as in U.S. Pat. No. 4,981,470, issued on Jan. 1, 1991 to Bombeck. This design still has the disadvantage that it is relatively large, expensive and difficult to produce. Also this design can only be used to monitor respiratory effort and not actual respiration.

Prior art to monitor respiratory effort also includes the use of a somewhat inflated balloon communicating with a pressure transducer via plastic tubing. The balloon is taped externally onto the stomach so that inspirations and expirations stretch the balloon thereby creating positive and negative pressure fluctuations in the tubing. The tubing communicates with the pressure transducer monitoring respiratory effort, rather than air flow. This method does not measure pressure changes due to movement of air in, or in the proximity of, the lung airways or the esophagus. This method is also less sensitive and more prone to errors due to body movement or badly taped sensors.

Prior art to measure respiration, that is actual movements of air in and out of the respiratory organs such as the nostrils, uses thermistors that monitor the temperature of respiratory air. This is based on the idea that inspiratory air is cooler than expiratory air. Such thermistors are not connected to pressure transducers. Alternatively, pneumotachographs exist where two pressure sensors in series monitor pressure drops over a resistor. This is used to calculate air flow and volume, which information is used in turn to calculate peak flow and tidal volumes. This method is, however, complicated and expensive and extends the breathing circuit.

Soviet Patent No. 272,477, issued on May 20, 1968 to Leya and Berzinsh, teaches a stomach-intestinal probe consisting of multiple antimony electrodes to measure stomach acids and a large inflatable balloon to fix the probe in the esophagus so that fluoroscopy can be used to watch the movement of the stomach. This probe permits simultaneous monitoring of stomach acid and stomach movements. However, the balloon is relatively large and blocks esophagus function, thus breaking normal sleep patterns. Also, the balloon cannot function as a pressure sensor since it is too large and not connected to an external pressure monitor.

German Patent No. 2,162,656, issued to Wolters and Eckert on Jun. 20, 1973, teaches a stomach acid gauge with an electrical pH sensor. Once again, this device does not measure respiratory effort. Similar one-function stomach acid sensors are taught by U.S. Pat. No. 4,618,929, issued on Oct. 21, 1986 to Miller et al., and by U.S. Pat. No. 4,176,659, issued on Dec. 4, 1979 to Rolfe.

U.S. Pat. No. 4,503,859, issued on Mar. 12, 1985, to Petty, et al., teaches a device to simultaneously monitor esophageal acid and heart EKG. This device does not measure respiratory effort in any way.

German Patent No. DE 3523987A, issued on Jan. 8, 1987 to Lange, teaches a method to measure stomach function consisting of multiple pH sensors attached to the outside of a balloon on a catheter. The balloon, however, is used only to inflate inside the stomach and thereby distribute the pH sensors against the stomach wall. Normal esophageal function is blocked and respiratory effort is not measured.

U.S. Pat. No. 4,681,116, issued on Jul. 21, 1987 to Settler, teaches an antimony electrode used as an esophageal electrode. This uses an epoxy resin as a sealant. This is also a single function device which does not simultaneously monitor respiratory effort.

Sleep apnea is the problem of inadequate breathing while asleep. It can have several causes, with each cause requiring different remedies. Hence, individual treatment of sleep apnea can follow only after study of the causes of sleep apnea in the individual.

One alternative cause of sleep apnea is gastroesophageal reflux (GER). GER is the process by which the subject generates acids in the stomach, which are then passed into the esophagus. These acids can then be aspirated into the lungs, causing a constriction of the trachea and difficulty in breathing. However, GER can also be a result, instead of a cause, of sleep apnea. Difficulty in breathing, caused by other reasons, can lead to increased respiratory effort in compensation. This increased effort can then encourage GER. In effect, this causes a sucking of the gastric acid into the esophagus from the stomach.

Yet other causes of apneas in the sleep apnea syndrome may be of neurological origin or, more often, from obstruction due to the collapse of the posterior pharyngeal wall during inspiration. Such obstruction may be partial and give rise to the snoring sound. In obstruction sleep apnea, the patient's respiratory efforts may not result in adequate movement of air into and out of the patient's lungs in spite of adequate respiratory efforts. Consideration of all of this is necessary when determining the cause of an individual's sleep apnea and the proper remedy.

It is an object of this invention to provide a method for monitoring respiratory effort in the upper gastrointestinal tract (the stomach and esophagus) distal to any nasal or pharyngeal obstructions, without using a balloon, which can be used as an alternative to the method forming the subject matter of prior U.S. patent application Ser. No. 07/972,208 now U.S. Pat. No. 5,477,860.

It is another object of this invention to provide a method for monitoring respiration and respiratory effort using a pair of catheters having the same or similar design but placing the monitoring site of one of the catheters (that is, the inlet to the catheter) proximal to a possible obstruction site.

It is another object of the invention to provide a method of determining the existence and location of an obstruction in a respiratory track which is suitably performed by appropriate first and second catheters.

It is a further object of the present invention to provide a catheter that monitors movements of air inside or in the immediate proximity of upper airways such as the nostrils (to measure respiration) and in the esophagus (to measure respiratory effort).

These and other objects and advantages of the present invention will become apparent from a reading of the attached specification and appended claims.

SUMMARY OF THE INVENTION

The present invention relates to an alternative method of determining the existence and location of an obstruction in a respiratory track. The method includes the operation of introducing a first catheter having a first sensing site into the body of a patient until the first sensing site is positioned so that it is distal to the obstruction. The first catheter is then used to monitor respiratory effort with generated signals indicative of respiratory effort. A second catheter having a second sensing site is positioned so that the second sensing site is near the nostrils. The second catheter is used to monitor actual respiration with generated signals indicative of the actual respiration. Existence of the obstruction is verified by observing respiratory effort signals without corresponding actual respiration signals.

The obstruction may be located by inserting the second catheter into the respiratory track until the signals indicative of actual respiration cease to occur. This indicates that the second catheter also has been pushed to a distal side of the obstruction. Alternatively, the obstruction can be located by withdrawing the first catheter until it registers respiration effort signals similar to actual respiration signals registered by the second catheter. This indicates that the first catheter has crossed over to a proximal side of the obstruction. The second catheter can be similar to the first catheter. The second catheter can be positioned just inside one of the nostrils of the patient.

The first catheter to can be used to monitor respiratory effort with any pressure sensor. For example, the pressure sensor may be either of an electrical pressure transducer located at the first sensing site, an optical pressure sensor located at the first sensing site, a lumen providing water perfusion at the first sensing site, a balloon pressure sensor, or an impedance sensor. An acoustic sensor can also be used. The second catheter can be used to monitor actual respiration with any pressure sensor, as described in the preceding sentence, an acoustic sensor, or with any temperature sensor. For example, the second catheter may use an electrical pressure transducer located at the second sensing site, an optical pressure sensor located at the second sensing site, a lumen providing water perfusion at the second sensing site, a balloon pressure sensor, an impedance sensor, or a thermistor located at the second sensing site. An acoustic sensor can also be used.

DESCRIPTION OF THE PREFERRED EMBODIMENTS

Figure 1:
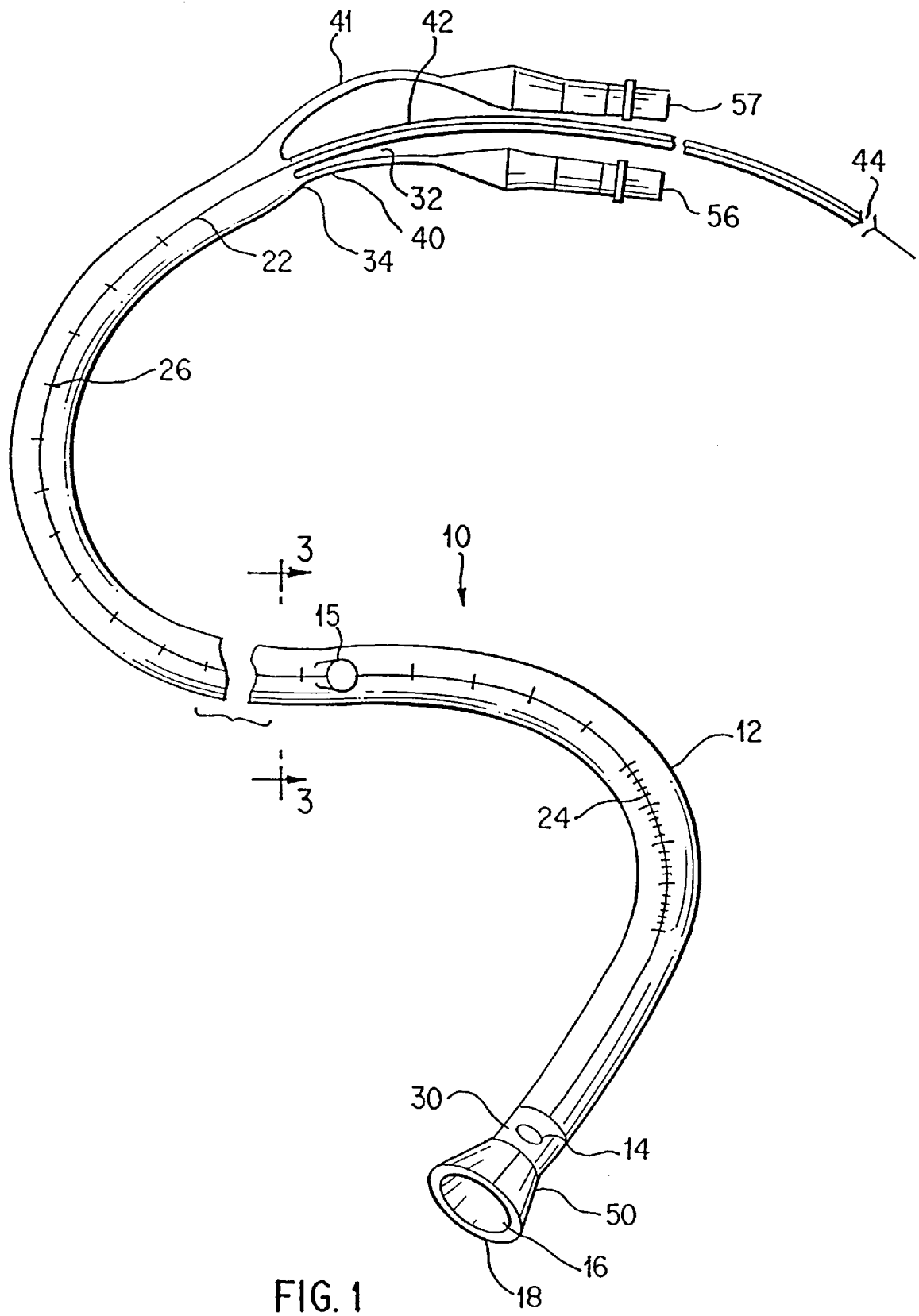
FIG. 1 is a diagrammatic side view of a catheter which can be used in accordance with a method to which the present invention is an alternative.

FIG. 1 shows a catheter 10 which comprises a tubular body 12, a pH sensor 14, an opening 15 for interior communication with an air pressure monitor and recorder for respiration and an opening 16 for interior communication with an air pressure monitor and recorder for respiratory effort. The pH sensor 14 is connected to an electrical conductor that extends through the interior of the tubular body 12 so as to provide for pH measurement close to the distal end 18.

The tubular body 12 of the catheter 10 is a three lumen catheter having an outer diameter of approximately 2.1 millimeters. The tubular body 12 is comprised of a clear polyvinyl chloride (PVC) material. The interior surfaces of the lumens are lined with TEFLON. The tubular body 12 includes a red radiopaque stripe 22 extending longitudinally for the entire length of catheter 10. This radiopaque stripe 22 should be of a type that can be easily seen during fluoroscopy.

The tubular body 12 is marked circumferentially with gradations 24. These gradations preferably occur in one centimeter increments. All of these markings are relative to the distance from the distal tip 18 of the catheter 10. Every fifth circumferential mark has a slightly thicker band 26 and is appropriately numbered. The markings and numberings start at the five centimeter mark from the distal tip 18 and proceed approximately to forty centimeters. These markings allow the use of the catheter 10 to appropriately position the catheter within the body of the patient and to make approximations as to the location of the catheter within the body.

The pH sensor 14 comprises a head portion 30 that is inserted in the catheter close to the distal end of the tubular body 12. The pH sensor further comprises a conductor 32 that is connected to the head portion 30 and extends from the head portion 30 to the proximal end 34 of the tubular body. The head portion 30 is of a polycarbonate material having a smooth surface. The pH sensor of the present invention is a monocrystant antimony pH sensor. The head portion 30 is of the same diameter as the tubular body 12 so that there are no sharp edges. A longitudinal hole in the head portion 30 allows free communication of pressure changes through the lumen that measures respiratory effort from the hole in the head portion 30 to the proximal end 56 of the same lumen. The head portion 30 is fixed in place in the tubular body 12 by ultrasonic or vibration bonding. The head portion 30 and the widening end piece 50 have an interior channel connecting the opening 16 to a lumen to provide a continuous air channel from opening 16 to the proximal end of the catheter.

The pH sensor 14 and the opening 16 for monitoring of respiratory effort should be installed in such a way that the pH sensor 14 and the opening 16 remain separated. Ideally, this separation should be at least three centimeters. The reason for this separation is to allow the esophagus ample room to contract around the catheter body, and clear residual GER away from the pH sensor.

The tubular body 12 should have a length of approximately fifty centimeters. The proximal end 34 of the catheter 10 should be broken out into three clear polyvinyl chloride leads 40, 41 and 42. The pH sensor channel lead 42 should have a length of approximately seventy centimeters and an inner diameter of 0.9 millimeters. The pH portion of the catheter 10 will thus have an overall length around one hundred and twenty centimeters. The conductor 32 for the pH sensor 14 should be TEFLON coated. This conductor 32 is to be threaded through the pH sensor lumen of the catheter 10, through the pH channel lead, and terminated with a male tip plug connector 44. The pH sensor conductor 32 is secured to plug 44. Plug 44 may then be connected to an appropriate monitor for monitoring acidity conditions within the esophagus.

The opening 16 for monitoring the respiratory effort comprises a widening 50 of the catheter that is molded onto the tubular body 12. In addition, the opening 16 for monitoring respiratory effort leads to an air pressure communication lumen that extends through the interior of the tubular body 12 and the head portion 30 such that the lumen communicates through opening 16 to lead 40.

As will be described hereinafter, the air pressure communication lumen leads 40 and 41 are TEFLON-lined. The lumen leads 40 and 41 are connected to plugs, or female luer locks, 56 and 57 that may be attached to an adjacent air pressure monitor and recorder, external to the catheter. The lumen leads 40 and 41 should have a length of 20 centimeters and an inner diameter of approximately 0.9 millimeters. The channel leads 40 and 41 should be made of TEFLON and have a cross-sectional configuration such that the leads 40 and 41 will not kink. The leads 40 and 41 are terminated with the female luer locks 56 and 57. The ports or openings 16 and 15 are widened to about 1.3 millimeters to prevent clogging in the catheter.

Figure 2:
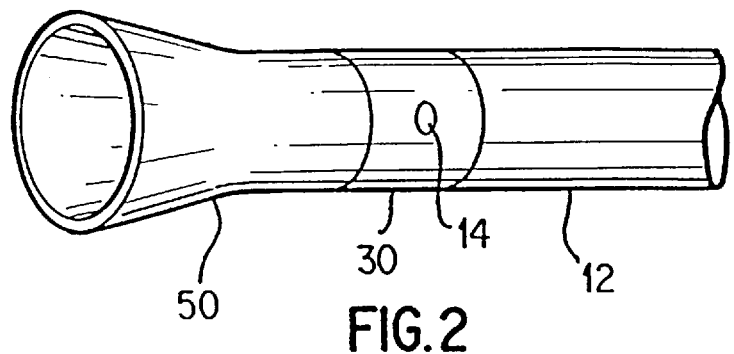
FIG. 2 is an end view of the catheter shown in FIG. 1.

Referring to FIG. 2, there is shown an end view of the catheter 10. Specifically, in this end view, there is shown the widening end piece 50 of the catheter that is mounted on head portion 30. The head portion 30 is of a polycarbonate material. The electrical conductor (not shown) from the pH sensor is inside of the head portion 30, and is connected to the end of the pH sensor 14. The tubular body 12 is attached to the head portion 30 which, in turn, is attached to the widening end piece 50 of the catheter by ultrasonic or vibration bonding. Since the instruments shown in FIGS. 1–4 and according to the present invention are to be used in internal medicine, it is important to avoid adhesives and other bonding agents.

Figure 3:
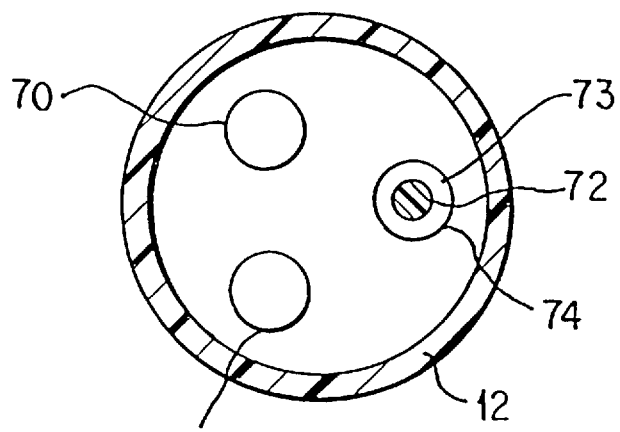
FIG. 3 is a cross-sectional view along line 3—3 of FIG. 1.

FIG. 3 shows a cross-section view of the internal configuration of catheter 10 proximal to the opening 15 that communicates with the pressure sensor for monitoring of respiration via lead 41. There are three lumens 70, 71 and 73. Lumen 73 contains the conductor 72 for the pH sensor 14 (shown in FIG. 1). Conductor 72 is coated with TEFLON material 74. This TEFLON-coating allows the conductor to be easily threaded through the lumen 73 within the catheter 10. This conductor is threaded through the lumen 73 of the catheter 10, through the pH lumen lead 42 (as shown in FIG. 1) and eventually terminates with plug 44 (see FIG. 1). The lumen 73 (the pH sensor channel) must be large enough to accommodate the TEFLON coated wire 72. Lumens 70 and 71 should have a diameter of 0.9 mm to allow adequate air flow communication from openings 15 and 16 through the lumens 70 and 71 to channel ends at connectors 56 and 57. The walls of channel lumens 70 and 71 should be TEFLON-lined in order to increase resistance to radial deformation and to reduce air flow resistance. FIG. 3 also shows the inclusion of the red radiopaque stripe 22 as formed on the clear polyvinyl chloride tubular body 12.

In operation as a single lumen variation, the distal end opening 16 on catheter 10, without opening 15 and without pH sensor 14, communicates with the lumen's proximal end, where an air pressure sensor is connected to the air channel lumen communicating with opening 16 to monitor respiratory effort or respiration. When the catheter is properly placed in the esophagus (where negative pressure is created during an inspiratory effort and positive pressure is created during an expiratory effort), it is possible to monitor respiratory effort and its direction (respiratory or inspiratory). If, on the other hand, opening 16 (or if a two channel catheter is used, opening 15), is placed in proximity of the nostrils, movement of air is measured with this lumen, and actual respiration (or inspiration) is measured. In a two lumen variation, opening 15 communicates through a lumen separate from opening 16, to a separate air pressure monitor and recorder. If, in the case of a two lumen probe, opening 16 is placed distal to a nasopharyngeal obstruction and opening 15 is placed proximal thereof, then lack of a respiration signal in the presence of a respiratory effort signal indicates the obstruction.

With a pH sensor attached, it is possible to correlate apneas and respiratory efforts with GER. This can be done by simultaneous measurement of three factors (GER, respiration, and respiratory effort) with one catheter.

Figure 4:
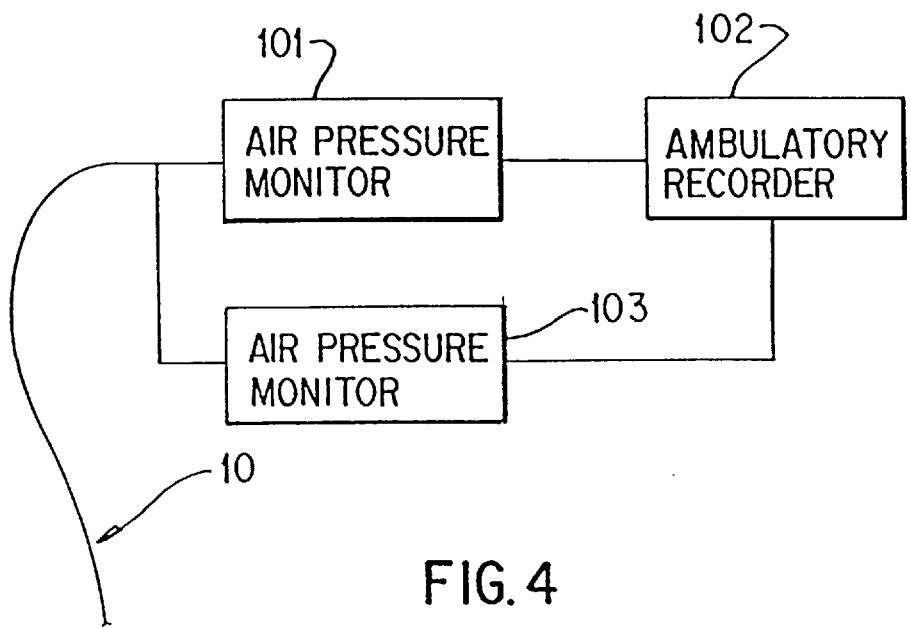
FIG. 4 shows a catheter attached to two air pressure monitors which are attached to an ambulatory recorder.

FIG. 4 shows the catheter 10 attached to two air pressure monitors 101 and 103, which are attached to an ambulatory recorder 102. A separate external ambulatory air pressure monitor is connected to each air communication lumen in the catheter 10 (in this figure, two monitors, for a two lumen catheter 10, are shown). Each monitor 101 and 103 monitors the changes in air pressure at the site of the distal opening of each air communication lumen in the catheter 10. Each monitor 101 and 103 is connected to a common ambulatory recorder 102 to record the air pressure readings from each monitor 101 and 103. The whole system of the catheter 10, the monitors 101 and 103, and the recorder 102, is ambulatory.

Figure 5:
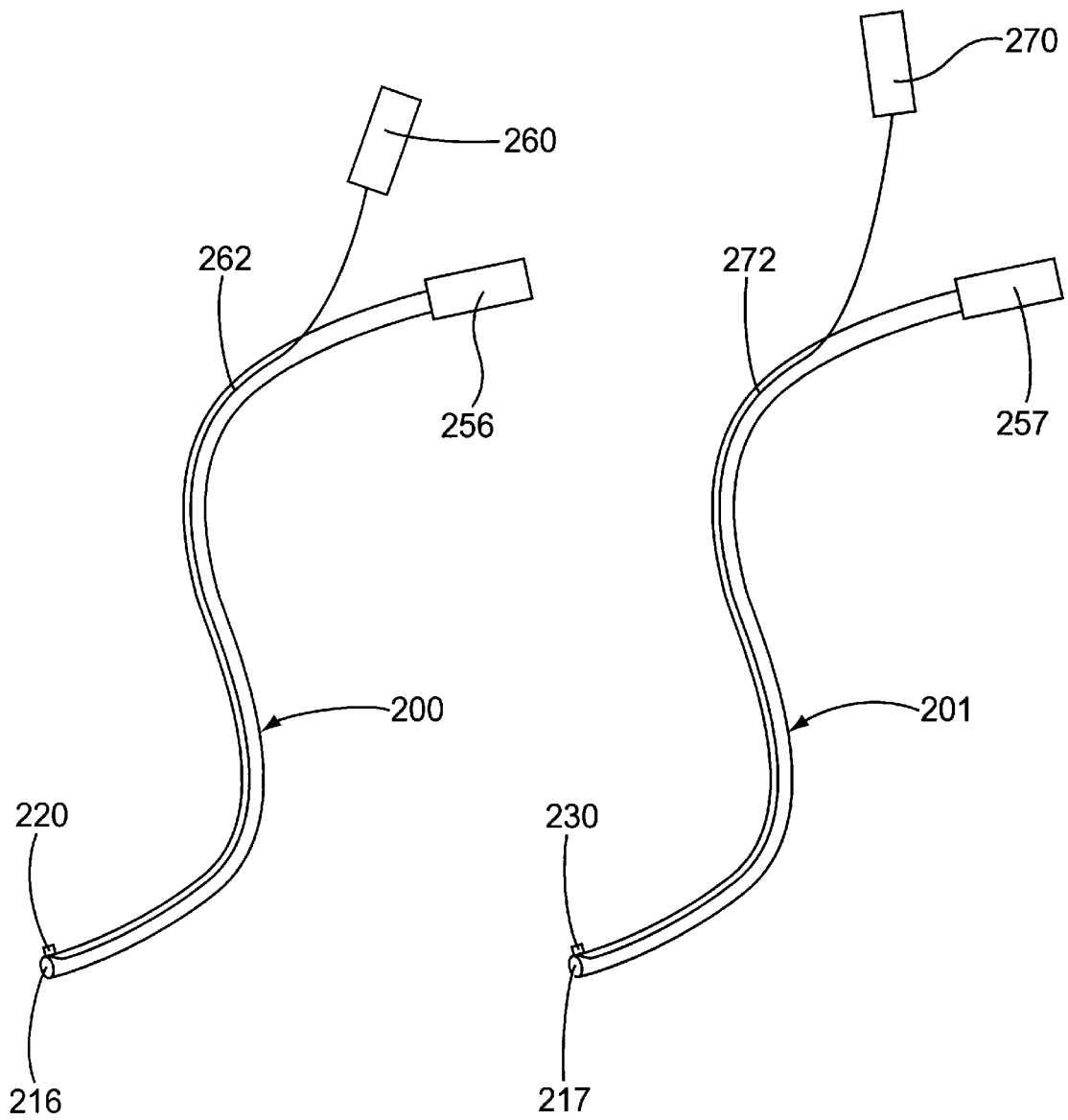
FIG. 5 shows first and second catheters which can be used in the method forming the subject matter of the present invention.

FIG. 5 shows a construction by which the method forming the subject matter of the present invention can be carried out. Two catheters 200 and 201, each of which may be of the single lumen variation mentioned previously, are utilized. Such catheters, typically, are designed to provide perfusion at distal lumen openings thereof. The method of determining existence and location of an obstruction in a respiratory track, according to the present invention, includes the operations of introducing the first catheter 200 having a first sensing site, including a first distal lumen opening 216, into the body of a patient and positioning the first sensing site so that the first sensing site is distal to the obstruction. Typically, perfusion of water or another suitable liquid through the opening 216 is provided. Perfusion at the first sensing site through the opening 216 correlates with a local pressure. The local pressure, in turn, directly corresponds to respiratory effort. Variations in perfusion, such as variations in liquid flow rates, at the first sensing site, therefore, constitute signals indicative of respiratory effort. In this way, the first catheter 200 can be used to monitor respiratory effort with the signals generated at the first sensing site which are indicative of respiratory effort. A second catheter 201 having a second sensing site, including a second distal lumen opening 217, is positioned so that the second sensing site is near the nostrils of the patient. The second catheter 201 is used to monitor actual respiration. Signals, indicative of actual respiration, may be generated based on variations in perfusion at the second sensing site in a manner similar the way signals are generated at the first sensing site. The existence of the obstruction is verified by observing respiratory effort signals without corresponding respiration signals.

Each of the catheters 200 and 201 could include an air channel lumen rather than a perfusion lumen, which air channel lumen may or may not have a balloon (not shown) at the distal opening, comprising a balloon pressure sensor arrangement. As was described previously in connection with the catheter represented in FIGS. 1–3, respiratory effort and respiration could then be monitored by air pressure sensors communicating with the air channel lumens.

Alternately or, if desired, additionally, the first sensing site can include a known pressure sensor 220 disposed on the first catheter 200 near the first distal opening 216. Similarly, the second sensing site can alternately or, if desired, additionally include a known pressure sensor 230 disposed on the second catheter 201 near the second distal opening 217. Each of the sensors 220 and 230 could be either a known optical pressure sensor including, for example, an optical fiber or a known electric pressure sensor, i.e. a pressure transducer. The sensor 220 disposed on the first catheter 200 could also be either a known acoustic or a known impedance sensor. The first catheter 200, moreover, could utilize a known pressure indicating balloon pressure sensor at the first sensing site in place of, or in addition to, the sensor 220. Additionally, at least the actual respiration monitoring sensor 230 disposed on the second catheter could be a known electrical resistor making use of a semiconductor having a resistance which varies in a known manner with temperature, i.e. a thermistor. This is because, as noted previously, inspiratory air is cooler than expiratory air. The sensor 220 is connected to a known output connection 260 by a known connector 262, such as a TEFLON coated electrically conducting wire, extending either through the single lumen or, if desired, through a second lumen defined in the first catheter 200, while the sensor 230 is connected to a known output connection 270 by a known connector 272, such as a TEFLON coated electrically conducting wire, extending either through the single lumen or, if desired, through a second lumen defined in the second catheter 201. The signals generated at the sensing sites by the sensors 220 and 230 can thus be transmitted, by the output connections 260 and 270 and the connectors 262 and 272, to an appropriate output device located externally of the catheters 200 and 201. In this way, the generated signals permit using the catheters 200 and 201 to monitor respiratory effort and actual respiration.

The first catheter 200 has a solid cylindrical wall, is hollow throughout, and has its proximal end connected to a connection 256. If the first catheter 200 is of the type including an air channel lumen, then the connector 256 is a plug similar to the plug or female luer lock 56 shown in FIG. 1. The second catheter 201 has a solid cylindrical wall, is also hollow throughout, and has its proximal end connected to a connector 257. If the second catheter is of the type including an air channel lumen, then the connector 257 is a plug similar to the plug or female luer lock 57 shown in FIG. 1. These plugs 256 and 257, in this case, are attached to an external pressure transducer and monitor as mentioned previously.

Each of the catheters 200 and 201 may include gradations and be constructed of material similar to the tubular body 12 shown in FIG. 1. The lengths and diameters of the catheters 200 and 201, moreover, are similar to those of the tubular body 12. Again, the plug 256 or 257 at the proximal end of the communication channel defined in the catheter 200 or 201 is suitable for connection to an air pressure monitor and recorder external to the patient.

The obstruction can be located by inserting the second catheter 201 into the respiratory track until the signals indicative of actual respiration cease to occur. This provides an indication that the second catheter 201 has been pushed to a distal side of the obstruction.

The obstruction can alternatively be located by withdrawing the first catheter 200 until it registers respiration effort signals similar to respiration signals registered by the second catheter 201. This provides an indication that the first catheter has crossed over to a proximal side of the obstruction.

Preferably, the second catheter 201 is similar to the first catheter 200. The second catheter 201 can be positioned just inside one of the nostrils.

Observation of the respiratory effort signals may be performed by monitoring pressure through the opening 216 defined at the first sensing site. Actual respiration can be monitored by using the second catheter 201 to monitor pressure through the opening 217 defined at the second sensing site.

In the study of sleep apnea, the present invention allows measurement of the parameters of respiration and respiratory effort, including their inter-relationships. The instruments shown in FIGS. 1–4 and according to the present invention allow these measurements to be taken simultaneously. The catheters of the present invention are of such a small diameter that they do not disturb normal sleep or other bed activity. As such, the present invention allows the effective study and analysis of sleep apnea that has until now eluded medical science.

Some variations in the particular methods of determining the existence and location of an obstruction in a respiratory track described above are possible. For example, such a method could include the steps of introducing a multisite pressure sensor catheter so that some sensors are positioned at sites distal to the obstruction and some sensors are positioned at sites proximal to the obstruction, and verifying existence and location of the obstruction by comparing respiratory effort signals from the different sensors at the different pressure sensing sites. Obstructive and central nervous system sleep apnea, or central apnea, moreover, can be monitored by introducing into a respiratory track a first sensor catheter and positioning its sensor distal to any airway obstruction for monitoring respiratory effort, positioning in the respiratory track a second sensor catheter so that its sensor is sufficiently near nostrils to permit monitoring of actual respiration, connecting the catheters to an ambulatory recorder and recording signals from the sensors and thus monitoring both respiratory effort and respiration, and classifying recorded apneas as obstructive if respiratory efforts do not result in air flow and as central nervous system, or central, if there is no respiratory effort. An alternative method of monitoring obstructive and central nervous system sleep apnea, or central apnea, may include the operations of using one sensor system for detecting respiratory effort and another sensor system for detecting respiration, connecting the sensor systems to an ambulatory recorder and recording signals from the systems, and classifying recorded apneas as obstructive if respiratory efforts do not result in airflow and as central nervous system, or central, if there is no respiratory effort. The sensor systems in this method can be, for example, any of the applicable catheter arrangements described in this invention disclosure.

The embodiment illustrated and discussed in the specification is intended only to teach to those skilled in the art the best way known by the inventor to make and use the invention. Nothing in the specification should be considered as limiting the scope of the present invention. Changes could be made by those skilled in the art to produce equivalent systems without departing from the invention. The present invention should only be limited by the following claims and their legal equivalents.

For example, any combination of pressure sensor sites (one, two or more) with other sensors may be used. Also, the resulting information regarding pressures and other variables may be monitored, recorded, processed and displayed in different manners once collected by the catheter.

I claim:

1. A method of determining existence and location of an obstruction in a respiratory track comprising the steps of:

introducing a first catheter into the respiratory track so that a first sensing site is positioned distal to the obstruction, by inserting the first catheter into the respiratory track until signals from the first catheter indicative of respiratory effort cease to occur, indicating that the first catheter has been pushed to a distal side of said obstruction;

using the first catheter to monitor respiratory effort with signals generated at said first sensing site indicative of the respiratory effort;

positioning a second catheter in the respiratory track so that a second sensing site is near nostrils;

using the second catheter to monitor actual respiration with signals from the second catheter generated at said second sensing site indicative of the actual respiration; and verifying existence of the obstruction by observing respiratory effort signals without corresponding actual respiration signals.

2. A method as defined by claim 1, wherein said step of using the first catheter to monitor respiratory effort includes the step of using a sensor selected from the group consisting of:

a pressure transducer;

an optical pressure sensor;

a lumen providing perfusion;

an acoustic sensor;

a balloon pressure sensor; and an impedance sensor.

3. A method as defined by clam 1, wherein said step of using the second catheter to monitor actual respiration includes the step of using a sensor located at said second sensing site to monitor said actual respiration, where the sensor is selected from the group consisting of a pressure sensor and a temperature sensor.

4. A method as defined by claim 3, wherein said pressure sensor is selected from the group consisting of a pressure transducer, an optical pressure sensor, or a lumen providing perfusion, and said temperature sensor is a thermistor.

5. A method as defined by claim 1, further comprising the step of locating the obstruction by inserting the second catheter into the respiratory track until the signals indicative of actual respiration cease to occur, indicating that the second catheter also has been pushed to a distal side of said obstruction.

6. A method as defined by claim 1, further comprising the step of locating the obstruction by withdrawing the first catheter until it registers respiration effort signals similar to respiration signals registered by the second catheter, indicating that the first catheter has crossed over to a proximal side of said obstruction.

7. A method of determining existence and location of an obstruction in a respiratory track comprising the steps of:

introducing a first sensor catheter into the respiratory track and positioning the catheter so that a first sensor on the first catheter is positioned distal to the obstruction thus monitoring respiratory effort, by inserting the first catheter into the respiratory track until signals from the first sensor indicative of respiratory effort cease to occur, indicating that the first sensor has been pushed to a distal side of said obstruction;

positioning a second sensor catheter in the respiratory track so that a sensing site on the second catheter is sufficiently near nostrils to permit monitoring signals indicative of actual respiration; and verifying existence of the obstruction by observing respiratory effort signals without corresponding respiration signals.

8. A method as defined by claim 7, further comprising the step of locating the obstruction by inserting the second sensor catheter into the respiratory track until respiration signals similar to the respiratory effort signals cease to occur, indicating that the second sensor catheter also has been pushed to a distal side of said obstruction.

9. A method as defined by claim 7, further comprising the step of locating the obstruction by withdrawing the first sensor catheter until it registers respiration effort signals similar to respiration signals registered by the second sensor catheter, indicating that the first sensor catheter has crossed over to a proximal side of said obstruction.

10. A method as defined by claim 7, wherein said second sensor catheter has a structure the same as said first sensor catheter.

11. A method as defined by claim 7, wherein said sensor catheters include sensors which are any of a pressure sensor, a temperature sensor, an electrical pressure transducer, an optical pressure sensor, and a thermistor.

12. A method as defined by claim 7, wherein the step of positioning said second sensor catheter includes positioning said second sensor catheter just inside one of the nostrils.

13. A method of monitoring obstructive and central nervous system sleep apnea comprising the steps of:

introducing into a respiratory track a first sensor catheter and positioning a sensor on the first catheter distal to any airway obstruction for monitoring respiratory effort;

positioning in the respiratory track a second sensor catheter so that a sensor on the second catheter is sufficiently near nostrils to permit monitoring of actual respiration;

connecting the catheters to an ambulatory recorder and recording signals from the sensors and thus monitoring both respiratory effort and respiration;

recording an apnea when there are no signals indicative of actual respiration and classifying recorded apneas as obstructive if signals indicative of respiratory efforts occur in the absence of signals indicative of actual respiration and as central nervous system if there are no signals indicative of respiratory effort and no signals indicative of actual respiration.

* * * * *